United States Patent [19]
Reid et al.

[11] Patent Number: 4,756,820
[45] Date of Patent: * Jul. 12, 1988

[54] METHOD FOR RETARDING CORROSION AND COKE FORMATION AND DEPOSITION DURING PYROLYTIC HYDROCARBON PROCESSING

[75] Inventors: Dwight K. Reid, Houston; David R. Forester, The Woodlands, both of Tex.

[73] Assignee: Betz Laboratories, Inc., Trevose, Pa.

[*] Notice: The portion of the term of this patent subsequent to May 5, 2004 has been disclaimed.

[21] Appl. No.: 883,254

[22] Filed: Jul. 8, 1986

Related U.S. Application Data

[63] Continuation-in-part of Ser. No. 773,402, Sep. 6, 1985, Pat. No. 4,680,421.

[51] Int. Cl.$^4$ .............................................. C10G 9/12
[52] U.S. Cl. ..................... 208/48 AA; 208/48 R; 208/50; 208/131; 423/276; 423/277; 423/279; 585/950; 252/389.4; 252/389.41; 252/182.32
[58] Field of Search ......... 208/48 R, 131, 50, 48 AA; 423/276, 277, 279; 585/950; 252/182, 389.4

[56] References Cited

U.S. PATENT DOCUMENTS

| 1,847,095 | 3/1932 | Mittasch et al. | 208/48 R |
|---|---|---|---|
| 3,087,936 | 4/1963 | LeSuer | 252/389.4 |
| 3,228,884 | 1/1966 | Daignault | 252/389.4 |
| 3,262,961 | 7/1966 | Jordan | 252/389.4 |
| 3,328,119 | 6/1967 | Robson | 423/277 |
| 3,381,051 | 4/1968 | Bergier et al. | 208/48 R |
| 3,507,929 | 4/1970 | Happel et al. | 585/950 |
| 3,531,394 | 9/1970 | Koszman | 208/48 R |
| 3,536,776 | 10/1970 | Neng | 208/48 R |
| 3,687,840 | 8/1972 | Sze et al. | 208/131 |
| 3,876,527 | 4/1975 | Dugan et al. | 585/950 |
| 3,948,759 | 4/1976 | Kiny et al. | 208/131 |
| 4,440,656 | 4/1984 | Horodysky | 252/389.4 |
| 4,533,481 | 8/1985 | Jahnke | 252/389.4 |
| 4,555,326 | 11/1985 | Reid | 208/48 R |
| 4,663,018 | 5/1987 | Reid et al. | 208/50 |

FOREIGN PATENT DOCUMENTS

| 229854 | 10/1963 | Australia | 208/48 R |
|---|---|---|---|
| 1254529 | 4/1976 | Fed. Rep. of Germany | 208/131 |
| 0021704 | 3/1973 | Japan | 252/389.1 |
| 1275662 | 8/1928 | United Kingdom | 208/48 R |
| 296752 | 6/1929 | United Kingdom | 208/48 R |
| 1385888 | 3/1975 | United Kingdom | 252/389.1 |

OTHER PUBLICATIONS

Starshov et al., Irv Vyssh. Ucheb., Neft 6A2, 1977, (Chem. Abs., vol. 87: 154474R).
Nikonov et al., USSR 834107, 1981, (Chem. Abs. 95: 135651v).
Storshov et al., Nfte Khimiya, 1979, (Chem. Abs.: 92: 8645j).

*Primary Examiner*—H. M. S. Sneed
*Assistant Examiner*—Helane Myers
*Attorney, Agent, or Firm*—Alexander D. Ricci

[57] ABSTRACT

The present invention is directed to a method of reducing fouling and corrosion in furnaces during the thermal cracking of hydrocarbons. The method generally comprises adding to the hydrocarbon an effective amount of boron or boron compounds. The preferred boron materials are the oxides, borates, borate esters, peroxyborates, boranes, organoboranes, borazine and salts of boron oxides. The oxides, borates or salts thereof, are preferable in non-mono-alcohol solvents.

22 Claims, No Drawings

METHOD FOR RETARDING CORROSION AND COKE FORMATION AND DEPOSITION DURING PYROLYTIC HYDROCARBON PROCESSING

This Application is a continuation-in-part of Application Ser. No. 773,402 filed Sept. 6, 1985 now U.S. Pat. No. 4,680,421.

BACKGROUND OF THE INVENTION

The present invention is directed to a method and composition for use in inhibiting the formation and deposition of coke on surfaces and corrosion of these surfaces during the elevated temperature processing of hydrocarbons. Coke deposition and corrosion are generally experienced when hydrocarbon liquids and vapors contact the hot metal surfaces of the processing equipment. While coke formation is perhaps not entirely technically understood, because of the complex makeup of the hydrocarbons, the hydrocarbons at elevated temperatures and in contact with hot metallic surfaces undergo various changes through either chemical reactions and/or decomposition of various unstable components of the hydrocarbon. The undesired products in many instances include coke, polymerized products, deposited impurities and the like. Whatever the undesired product that may be formed, the result is the same, i.e., reduced economies of the process. If these deposits are allowed to remain unchecked, heat transfer, throughput and overall productivity are detrimentally affected. Moreover, downtime is likely to be encountered due to the necessity of either replacing and/or cleaning of the affected parts of the processing system.

While the formation and type of undesired products are dependent upon the hydrocarbon being processed and the conditions of the processing, it may generally be stated that such products can be produced at temperatures as low as 100° F.; but are much more prone to formation as the temperature of the processing system and the metal surfaces thereof in contact with the hydrocarbon increase. At these temperatures, coke formation is likely to be produced regardless of the type hydrocarbon being charged. The type coke formed, i.e., amorphous, filamentous or pyrolytic, may vary somewhat; however, the probability of the formation of such is quite high.

As indicated in U.S. Pat. Nos. 3,531,394 and 4,105,540 the teachings of which are incorporated herein by reference, coke formation and deposition are common problems for example in ethylene (olefin) plants which operate at temperatures where the metal surfaces in contact with the hydrocarbon are at 1600° F. and above. The problem is prevalent in the cracking furnace coils as well as in the transfer line exchangers where pyrolytic type coke formation and deposition is commonly encountered. Ethylene plants, often referred to generally as "olefin plants", originally produced simple olefins such as ethylene, propylene, butenes and butadiene from a feed of ethane, propane, butanes and mixtures thereof. Later developments in the area of technology, however, have led to the cracking of heavier feedstocks because of their availability to produce aromatics and pyrolysis gasoline as well as light olefins. Feedstocks now include light naphtha and gas oil.

According to the thermal cracking processes utilized in olefin plants, the feedstocks in olefin plants are cracked generally in the presence of steam in tubular pyrolysis furnaces. The feedstock is preheated, diluted with steam and the mixture heated in the pyrolysis furnace to about 1500° F. and above, most often in the range of 1500° to 1650° F. The effluent from the furnace is rapidly quenched by direct means or in exchangers which are used to generate high pressure steam at 400 to 800 psig for process use. This rapid quench reduces the loss of olefins by minimizing secondary reactions. The cooled gas then passes to the prefractionator where it is cooled by circulating oil streams to remove the fuel oil fraction. In some designs, the gas leaving the quench exchanger is further cooled with oil before entering the prefractionator. In either case, the heat picked up by the circulating oil streams is used to generate steam and to heat other process streams. The moisture of gas and steam leaving the prefractionator is further cooled in order to condense the steam and most of the gasoline product in order to provide flux for the prefractionator. Either a direct water quench or heat exchanger are used for this cooling duty.

After cooling, cracked gas at or close to atmospheric pressure is compressed in a multistage compression system to much higher pressures. There are usually four or five stages of compression with interstage cooling and condensate separation between stages. Most plants have hydrocarbon condensate stripping facilities. Condensate from the interstage knockout drums is fed to a stripper where the $C_2$ hydrocarbons and lighter are separated. The heavier hydrocarbons are fed to the depropanizer.

While various treatments have been proposed to eliminate or reduce pyrolytic filamentous coke formation at elevated temperatures, none have attained any great degree of success. In the book "Coke Formation on Metal Surface" by Albright and Baker, 1982, methods are described which utilize silicon and aluminum as pretreatments. In accordance with the procedure, the furnace tubes are pretreated with silicon and aluminum hours before introduction of the hydrocarbon feedstocks. With the use of silicon, furnace tubes are coated by the chemical vaporization of an alkoxysilane. While U.S. Pat. Nos. 4,105,540 and 4,116,812 are generally directed to fouling problems in general, the patents disclose the use of certain phosphate and phosphate and sulfur containing additives for use purportedly to reduce coke formation in addition to general foulants at high temperature processing conditions.

With respect to coke retardation, various efforts have been reported, namely:

1. French Pat. No. 2,202,930 (Chem. Abstract Vol. 83, 30687K) is directed to tubular furnace cracking of hydrocarbons where molten oxides or salts of group III, IV or VIII metals (e.g., molten lead containing a mixture of $K_3VO_4$, $SiO_2$ and $NiO$) are added to pretreated charge of, for example, naphtha/steam at 932° F. This treatment is stated as having reduced deposit and coke formation in the cracking section of the furnace.

2. Starshov et al, *Izv Vyssh. Uchebn. Zaved., Neft GAZ,* 1977 (Chem. Abst. Vol. 87: 154474r) describes the pyrolysis of hydrocarbons in the presence of aqueous solutions of boric acid. Carbon deposits were minimized by this process.

3. Nikonov et al., U.S.S.R. No. 834,107, 1981; (Chem. Abst. 95: 135651v) describes the pyrolytic production of olefins with peroxides present in a reactor, the internal surfaces of which have been pretreated with an aqueous alcoholic solution of boric acid. Coke formation is not mentioned in this patent since the function of the boric acid is to coat the inner surface of the reactor and thus decrease the scavenging of peroxide radicals by the reactor surface.

4. Starshov et al., *Neftekhimiya* 1979 (Chem. Abst: 92: 8645j) describes the effect of certain elements including boron on coke formation during the pyrolysis of hydrocarbons to produce olefins.

5. U.S. Pat. No. 2,063,596 discusses in its prior art section the problems associated with the processing of hydrocarbons in equipment whose metallic parts have been supplied with a metalloid. The general impression is that such has not been utilized successfully.

6. U.S. Pat. No. 1,847,095 describes the metalloid compounds that are capable of yielding "volatile hydrogen" during the processing of hydrocarbons. The teachings of the patent are further limited in that reaction vessels composed of "Substances (free iron in particular) leading to deposition of soot should be absolutely excluded from the hot parts of the apparatus". In addition, although inner walls may be made of materials containing metalloids (quartz, ferro-silicon, mica and porcelain), addition of the hydrides of a metalloid are still required to inhibit coke formation. In fact, in the presence of silica gel as an example in that patent, hydrides of silicon were added to reduce coke formation. The patent is also notably silent with regards to the type of coke encountered and the problems associated therewith.

7. Baker, R. T. K., Gas Chem. Nucl. React. Large Indust. Plant, Proc. Conf., 1980. Chem. Ab. Vol. 94, 1981, 94: 814h, is directed to the role of various additives, e.g., $B_2O_3$ in effecting the growth rate of filamentous coke produced from the decomposition of $C_2H_2$ on Ni-Fe or Mo Catalysts. $B_2O_3$ is stated as being the only additive which failed to provide any significant reduction in the growth of the filaments.

In spite of the above, the industry's requirements for a cost-effective method to inhibit coke formation which was safe to handle, could be easily and conveniently added, and which would provide additional benefits as a corrosion inhibitor were never satisfied.

DESCRIPTION OF THE INVENTION

The invention is directed to the use of certain boron compounds and compositions containing such to inhibit the formation and deposition of coke on the heated metallic surfaces of the structural and associated parts of equipment processing such, without the attendant significant corrosion thereof. In the high temperature processing of hydrocarbons the temperature thereof can be from about 1375° to 1900° F., with the metallic surfaces of the processing equipment reaching from about 1600° to 2200° F. These temperatures are commonly encountered as earlier indicated in the olefin plants. In these systems the components of the furnace (pyrolytic) as well as the ancillary parts are commonly composed of ferrous metal. Iron, as well as iron alloys such as low and high carbon steel, and nickel-chromium-iron alloys are customarily used for the production of hydrocarbon processing equipment such as furnaces, transmission lines, reactors, heat exchangers, separation columns, fractionators, and the like.

Unexpectedly, the present inventors also discovered that certain boron compounds, and compositions containing such, were found to inhibit furnace degradation resulting from corrosion. They discovered that coking and corrosion during the high temperature cracking of hydrocarbons may be significantly reduced on the iron-based and nickel-based surfaces of processing equipment by adding to the hydrocarbon feedstock or charge before and/or during cracking, oxides of boron, boric acid containing a minimal amount of water (substantially free of water preferred), salts of boron oxides or organic boron compounds in compositions which vary depending on the boron compound used.

The inventors discovered that certain peculiarities were evident in producing the particular compositions to be used. This aspect will be more comprehensively described later in this description. Suffice it to indicate at this point that the efficacy of formulations was sensitive to the solvating or suspending medium used with boron compounds.

The boron oxide compounds are preferentially formulated using glycollic-type solvents, in particular ethylene glycol, propylene glycol, hexylene glycol and the like since they produce marketable and easily fed solutions. The boron compounds which are utilizable for the present purpose include oxides of boron, salts of boron oxides, organic boron compounds, e.g., alkyl borates. Illustrative of the boron oxide compounds are: metaborates, e.g., sodium, potassium, lithium metaborates, triethyl borate; trimethyl borate; borate salts such as sodium tetraborate, potassium tetraborate, lithium tetraborate; ammonium borates, e.g. ammonium biborate and ammonium pentaborate (subject matter of parent application); etc. Also utilizable are such compounds as the anhydrous and hydrated borates, borate esters, peroxoborates, boranes, organoboranes and borazines.

As earlier generally indicated, in producing compositions of this invention certain critical precautions are to be followed depending on the boron compound used.

If boron oxide or boric acid, or combinations of these, are used, the composition should be substantially free of mono-alcoholic solvents. The solvent or medium which may be used to formulate the boron oxide compounds or boric acid include the glycollic-type solvents. The coke-inhibiting properties of aqueous solutions or simply water solutions with boric acid appear to decrease with increasing water content. Although water may be used as the solvating medium, the anticoking properties of the boric acid compositions containing such appear to deteriorate.

The boron compounds such as the boron oxides may be dissolved in the glycol carriers with or without water in any proportion, to produce a product for use in any coke-formation prone environments to effectively eliminate or in the least minimize such. Other boron materials such as organoboron compounds may be added neat or dissolved in non-mono-alcoholic solvents. Coking and corrosion are significant problems and if left untreated will eventually shut the operation down.

While the above describes the use of various agents, e.g., boron compounds, solvents, etc., as single items in a given composition, it is contemplated that mixtures of the separate items may be used as long as they are compatible.

Typical formulations would be as follows:

| Ingredient | Actual | Range |
|---|---|---|
| Boron oxide, boron oxide compounds or boric acid | 10–15% | 1–50 |
| Ethylene glycol | 90–85 | 50–99 |
| Water may be substituted for ethylene | | |

| Ingredient | Actual | Range |
|---|---|---|
| glycol with exception of when boric acid is used | | |
| Borester (e.g., tri-n-octyl borate) | 10–100% | 1–100 |
| Xylene | 90–0% | 0–99 |
| Alkali earth boron salts (e.g., KBO$_2$) | 10–15% | 1–50 |
| Ethylene glycol | 90–85 | 50–99 |
| Water may be substituted for the ethylene glycol | | |

The treatment dosages again are dependent upon the severity of the coking problem, location of such, and of course, the amount of boron-based compound in the formulated product. Accordingly, the amount of formulated product to be added to a charge should be such to provide 0.1 ppm to 10,000 ppm, and preferably 0.5 ppm to 5000 ppm, of product to said hydrocarbon charge.

EXAMPLES

In order to establish the efficacy of the invention concept various tests were conducted utilizing a propane feedstock with dilution steam added to enhance cracking. The apparatus and procedure used for the testing were as follows:

APPARATUS

The High Temperature Fouling Apparatus (HFTA) consists of five sections which together closely simulate the actual field pyrolysis of hydrocarbons to make light olefins and the coke formed on the heated metal surfaces during the pyrolysis reaction.

The feed preheat section is built of 316 stainless steel tubing and fittings and this section allows the mixing of nitrogen gas with steam during the start-up and shutdown of the HFTA and the propane with steam during the actual test. Steam is supplied at 40 psig by a steam generator. Nitrogen or propane are obtained from compressed gas cylinders. The gases and steam are heated to about 400° F. at which point small amounts of water (blank test) or antifoulant are slowly injected into the stream by a syringe pump.

Following antifoulant injection, the gases flow through a coiled 316 SS tube inside an electrically heated furnace. With a furnace temperature (surface temperature) of approximately 1865° F., the gases have been heated to 1150°–1250° F. when they exit the furnace.

Following the furnace tube, the gases travel through the coker rod assembly. This section consists of a 316 SS rod which is electrically heated to 1500° F. while the gases flow around the heated rod inside a 316 SS shell. The rod is electrically heated through a silicon controlled rectifier (SCR), then through two 4 to 1 stepdown transformers in series to achieve a low voltage (3–4 volts), high current (~200 amps) heating of the rod. A temperature controller is used to achieve power control through the SCR to maintain a rod temperature of 1500° F.

On exiting the coker rod, the gases pass through a condenser coil and then two knock-out flasks in ice baths to remove the water (steam) from the product gases. The remaining entrained water vapor in the gases is removed by passing through drierite granules.

The specific gravity of the product gas is determined in a gas densitometer and the gases analyzed using gas chromatography to determine product yields. The remaining gases are vented through a safety hood exhaust.

TEST PROCEDURE

The furnace was turned on and the temperature thereof was stabilized at 1200° F. while feeding nitrogen and steam. Furnace temperatures were then slowly increased to 1800° F. over a period of ten minutes while the coke inhibitor or water (blank), as the case may be, was injected into the mixed gas/steam line prior to the furnace at about 400° F. gas temperature.

Then nitrogen feed was gradually switched to propane feed (about 2 minutes). The temperature of the furnace was then increased to about 1865° F. over an approximately 30-minute period. The product gases were analyzed by gas chromatography and the temperatures, flowrates, pressures and product gas gravity recorded every 35 minutes during the 160-minute test on propane/steam feed. Gases exit the furnace tube at about 1150°–1250° F. and exit the coker shell at about 975°–1000° F. temperatures.

During a normal 160-minute run, approximately 3200–3300 grams of propane were fed and 1500–2000 grams of steam (determined from the condensate collected) for hydrocarbon to steam ratios of about 1.6:1 to 2.2:1.

Following shutdown and cooling, the furnace tube and coker shell were cleaned and the coke collected and weighed.

The coke was burned to determine how much was non-coke (metal corrosion products). After a series of blanks (water) and antifoulant tests were conducted, a steam to coke relationship was determined for the blanks and the predicted cokes compared to actual cokes of the treatments to determine percent coke reduction.

The data collected from the experiments using propane/steam feed and injecting water during blank runs (control) of boron-based formulations during tests are set forth in the examples below.

EXAMPLE 1

A summary of the tests conducted, and the results obtained using the HTFA, are set forth in Table 1 below. The Mann-Whitney statistical procedure was utilized in analyzing the data to develop a particular expression of confidence level.

Boric acid, when formulated in an aqueous solution, did not appear to significantly decrease the rate of coke formation. The significant confidence level of the protection of the boric acid in water against coke formation was at 54%, far below the 95% level needed to confidently demonstrate efficacy.

Other boron compounds, specifically boron fluorides, were also not found to exhibit significant antifouling properties. However, organoboron compounds such as tri-n-octyl borate (borester 1), tri-hexylene glycol biborate (borester 2) and tri- (m,p) cresyl borate (borester 3) either neat or dissolved in xylene were found to inhibit coke formation.

From the data summarized in Table 1, it can be seen that boron oxide and boric acid formulations when formulated in glycollic solvents were particularly effective in reducing coke formation. The significance level of the protection data for the boron oxide in ethylene glycol and hexylene glycol is 0.00005 and 0.016; these significance levels imply that at a 99.995% and 98.4% confidence level, the treated run is indeed unlikely to coke as quickly or as much as an untreated run. A similar conclusion is applicable to boric acid in either ethylene glycol or hexylene glycol.

added with various fluids to the hydrocarbon/steam stream are set forth in Table 2 below.

An examination of the data summarized in Table 2

TABLE 1

THE EFFECT OF VARIOUS BORON FORMULATIONS ON INHIBITING COKE FORMATION

| | | | Coke Protection, % | | | Statistical Analysis Mann-Whitney | Boron Count | |
|---|---|---|---|---|---|---|---|---|
| Additive | Solvent | No. of Runs | Average | Standard Deviation | Range | Significance Level* | Average ppm | Range ppm |
| Blank | $H_2O$ | 56 | 6.1 | 64.0 | | — | 0 | — |
| $H_3BO_3$ | $H_2O$ | 6 | 20.5 | 33.6 | −34 58 | 0.460 | 21.3 | 9−30 |
| $NH_4BF_4$ | E.G. | 6 | 37.7 | 23.5 | 8 66 | 0.15 | 28.3 | 7−52 |
| $NH_4BF_4$ | $H_2O$ | 5 | 18.2 | 67.7 | −57 91 | 0.32 | 20.4 | 14−36 |
| $(C_4H_9)_2NH_2BF_4$ | E.G. | 4 | 22.3 | 40.9 | −39 46 | 0.35 | 29.5 | 11−47 |
| $(C_4H_9)_2NH_2BF_4$ | $H_2O$ | 1 | 61.0 | — | 61 | — | 9.0 | 9 |
| $B_2O_3$ | E.G. | 19 | 64.8 | 29.1 | 2 97 | 0.00005 | 51.5 | 20−84 |
| $B_2O_3$ | H.G. | 8 | 48.3 | 50.3 | −57 96 | 0.016 | 26.4 | 12−51 |
| $B_2O_3$ | Methanol | 2 | 82.5 | 17.7 | 70 95 | — | 13.0 | 13 |
| $H_3BO_3$ | E.G. | 4 | 58.3 | 37.5 | 13 92 | 0.033 | 39.5 | 21−66 |
| $H_3BO_3$ | Methanol | 2 | 54.0 | 4.2 | 51 57 | — | 7.5 | 7−8 |
| $H_3BO_3$ | H.G. | 8 | 36.0 | 55.4 | −52 90 | 0.050 | 16.0 | 8−30 |
| $H_3BO_3$ | Ethanol | 2 | 91.5 | 5.0 | 88 95 | | 7.5 | 7−8 |
| $KBO_2$ | E.G. | 1 | 72.0 | — | 72 | — | 29.0 | 29 |
| $KBO_2$ | $H_2O$ | 1 | 28.0 | — | 28 | — | 43.0 | 43 |
| Borester 1 | (neat) | 6 | 54.2 | 32.1 | −5 81 | 0.020 | 35.5 | 24−52 |
| Borester 1 | Xylene | 3 | 9.7 | 73.0 | −65 81 | — | 13.7 | 9−17 |
| Borester 2 | (neat) | 4 | 50.8 | 33.3 | 11 91 | 0.070 | 75.0 | 55−110 |
| Borester 2 | Xylene | 1 | 83.0 | — | 83 | — | 19.0 | 19 |
| Borester 3 | Xylene | 1 | 80.0 | — | 80 | — | 11.0 | 11 |

*If Significance Level is greater than 0.05, a diminished level of confidence to differentiate between the performance of a treated and untreated run exists.

EXAMPLE 2

In order to show the benefit of the invention as a corrosion inhibitor, the amount of metallic corrosion products was determined after each run using the HTFA described earlier. The amount of corrosion for blank runs, and the amount of corrosion measured when boron oxide, boric acid and other boron compounds are added with various fluids to the hydrocarbon/steam stream are set forth in Table 2 below.

reveals that when boron-based materials are formulated in mono-alcoholic media, the corrosivity increases markedly. This is evident by the nearly 6 to 8 fold increase in corrosion above that of an untreated average run. The boron compounds when formulated in glycolic-type solvents or water were found to reduce the degree of corrosion significantly.

TABLE 2

THE EFFECT OF VARIOUS BORON FORMULATIONS ON INHIBITING CORROSION

| Additive | Solvent | No. of Runs | Average Amount of Corrosion per run* gm | Standard Deviation | Statistical Analysis Mann-Whitney Significance Level |
|---|---|---|---|---|---|
| Blank | $H_2O$ | 56 | 0.88 | 0.79 | — |
| $B_2O_3$ | E.G. | 19 | 0.36 | 0.10 | 0.001 |
| $B_2O_3$ | H.G | 8 | 0.34 | 0.14 | 0.006 |
| $H_3BO_3$ | E.G. | $3^A$ | 0.23 | 0.03 | 0.027 |
| $H_3BO_3$ | H.G. | 8 | 0.44 | 0.14 | 0.034 |
| $H_3BO_3$ | $H_2O$ | $5^B$ | 0.34 | 0.12 | 0.001 |
| Borester 1 | (neat) | $5^C$ | 0.49 | 0.16 | 0.148 |
| Borester 1 | Xylene | 3 | $1.18^1$ | $0.55^1$ | — |
| Borester 2 | (neat) | 4 | 0.57 | 0.19 | 0.054 |
| Borester 2 | Xylene | 1 | $2.38^1$ | — | — |
| Borester 3 | Xylene | 1 | $2.72^1$ | — | — |
| $NH_4BF_4$ | E.G. | 6 | 0.44 | 0.12 | 0.001 |
| $NH_4BF_4$ | $H_2O$ | 5 | 0.29 | 0.07 | 0.0001 |
| $(C_4H_9)_2NH_2BF_4$ | E.G. | $3^D$ | 0.41 | 0.03 | 0.001 |
| $(C_4H_9)_2NH_2BF_4$ | $H_2O$ | 1 | $0.43^1$ | — | — |
| $KBO_2$ | E.G. | 1 | $2.31^1$ | — | — |
| $KBO_2$ | $H_2O$ | 1 | $0.06^1$ | — | — |
| $B_2O_3$ | Methanol | 2 | 5.20 | 0.16 | — |
| $H_3BO_3$ | Methanol | 2 | 7.46 | 1.02 | — |

TABLE 2-continued
THE EFFECT OF VARIOUS BORON FORMULATIONS ON INHIBITING CORROSION

| Additive | Solvent | No. of Runs | Average Amount of Corrosion per run* gm | Standard Deviation | Statistical Analysis Mann-Whitney Significance Level |
|---|---|---|---|---|---|
| H₃BO₃ | Ethanol | 2 | 5.87 | 2.90 | — |

[A]Using a Q-test, data from run no. 10 with furnace tube no. 13 was rejected.
[B]Using a Q-test, data from run no. 10 with furnace tube no. 12 was rejected.
[C]Using a Q-test, data from run no. 32 with furnace tube no. 7 was rejected.
[D]Using a Q-test, data from run no. 9 with furnace tube no. 13 was rejected.
[1]Data not normalized for condensate rate or run number. Insufficient data points to normalize. These data points are presented for completeness only and cannot be compared directly with those data points that have been normalized.
*Average corrosion is normalized for run number and condensation rate.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method for inhibiting the formation and deposition of coke on the metallic parts of the system during the high temperature processing of a hydrocarbon without attendant substantial corrosion of metallic parts in contact with said hydrocarbon being processed, which comprises adding to the hydrocarbon to be heated and processed at a temperature of from about 1375° to 1900° F. a monohydric alcohol-free boron compound selected from the group of boric acid, providing that said acid contains a minimal amount of water, boron oxide compounds, and organo boron compounds.

2. A method according to claim 1 wherein the hydrocarbon is mixed with steam for enhancement of the cracking thereof.

3. A method according to claim 1 wherein the boron compound is contained in a water, a glycollic, or water-glycollic carrier substantially free of monohydric alcohol.

4. A method according to claim 2 wherein the boron compound is contained in a water, a glycollic, or water-glycollic carrier substantially free of monohydric alcohol.

5. A method according to claim 3 wherein the boron compound is boron oxide.

6. A method according to claim 5 wherein the boron oxide is added to the feedstock in an amount so as to provide from about 0.1 to 5000 parts of boron per million parts of feedstock.

7. A method according to claim 6 wherein the hydrocarbon is mixed with steam for enhancement of the cracking thereof.

8. A method according to claim 6 wherein the glycollic carrier is ethylene glycol and/or propylene glycol.

9. A method according to claim 1 wherein the feedstock is ethane, propane, butanes, light naphtha, heavy naptha, gas oil or mixtures of same.

10. A method according to claim 9 wherein the boron compound is added to the feedstock in an amount so as to provide from about 0.1 to 5000 parts of boron per million parts of feedstock.

11. A method according to claim 10 wherein the boron compound is selected from boric acid and boron oxide.

12. A method according to claim 11 wherein the hydrocarbon is mixed with steam to enhance cracking thereof.

13. A method according to claim 12 wherein the borate is contained in a water, glycollic or water-glycollic carrier.

14. In a method of inhibiting the formation and deposition of pyrolytic coke on the heated metal surfaces of the structural and associated parts of a pyrolysis furnace without the attendant corrosion thereof, which furnace is being used to crack a petroleum feedstock to produce olefins, and said metal surfaces thereof having temperatures of about 1400° F. or above, which method comprises adding to the feedstock before and/or during cracking thereof a coke inhibiting amount of a monohydric alcohol free boron compound selected from the group consisting of boric acid, providing said acid contains a minimal amount of water; boron oxide compounds; and organo boron compounds.

15. A method according to claim 14 wherein the feedstock is ethane, propane or butanes or mixtures thereof.

16. A method according to claim 15 wherein the olefins produced are ethylene, propylene, butadiene and various mixtures thereof.

17. A method according to claim 16 wherein the hydrocarbon is mixed with steam for enhancement of the cracking thereof.

18. A method according to claim 17 wherein the boron compound is added to the feedstock in an amount so as to provide from about 0.1 to 5000 parts of boron per million parts of feedstock.

19. A method according to claim 18 wherein the boron compound is contained in a water, glycollic or water-glycollic carrier.

20. A method according to claim 19 wherein the boron compound is boric acid.

21. A method according to claim 19 wherein the boron compound is boron oxide.

22. A method according to claims 20 or 21 wherein the carrier is ethylene glycol.

* * * * *